US00PP29469P3

(12) United States Plant Patent
Bell

(10) Patent No.: US PP29,469 P3
(45) Date of Patent: Jul. 10, 2018

(54) BLUEBERRY PLANT NAMED 'RIDLEY 4609'

(50) Latin Name: ***Vaccinium* hybrid**
Varietal Denomination: Ridley 4609

(71) Applicant: Mountain Blue Orchards Pty Ltd., New South Wales (AU)

(72) Inventor: Ridley Bell, New South Wales (AU)

(73) Assignee: MOUNTAIN BLUE ORCHARDS PTY LTD, Lindendale, New South Wales (AU)

( * ) Notice: Subject to any disclaimer, the term of this patent is extended or adjusted under 35 U.S.C. 154(b) by 11 days.

(21) Appl. No.: 14/999,949

(22) Filed: Jul. 18, 2016

(65) Prior Publication Data

US 2017/0027092 P1 Jan. 26, 2017

Related U.S. Application Data

(60) Provisional application No. 62/282,017, filed on Jul. 22, 2015.

(51) Int. Cl.
*A01H 5/08* (2018.01)

(52) U.S. Cl.
USPC ..... Plt./157

(58) Field of Classification Search
USPC ..... Plt./156, 157
See application file for complete search history.

(56) References Cited

U.S. PATENT DOCUMENTS

PP22,778 P3 6/2012 Wright et al.

*Primary Examiner* — Susan McCormick Ewoldt
*Assistant Examiner* — Karen M Redden
(74) *Attorney, Agent, or Firm* — Hahn Loeser & Parks, LLP

(57) ABSTRACT

The new blueberry plant variety 'RIDLEY 4609' is provided. The variety is produced from a cross of 'C95-152' (unpatented) and pollen parent 'C00-09' (U.S. Plant Pat. No. 22,778), which can be distinguished by its outstanding features.

6 Drawing Sheets

Latin name of genus, and species:
Genus—*Vaccinium.*
Species—hybrid.
Variety denomination: The new blueberry plant claimed is of the variety denominated 'RIDLEY 4609'.

STATEMENT REGARDING FEDERALLY-SPONSORED RESEARCH AND DEVELOPMENT

None.

BACKGROUND OF THE INVENTION

The present invention relates to a new and distinct perennial variety of *Vaccinium* hybrid (Southern Highbush Blueberry), which has been given the variety denomination of 'Ridley 4609'. Its market class is that of a fruiting plant. 'Ridley 4609' is intended for use as fresh fruit for shipping, customer pick and processing markets and as a home garden plant.

The new *Vaccinium* hybrid cultivar is a selection resulting from seedlings produced in a breeding programme of *Vaccinium* at Lindendale, NSW, Australia in August 2006 from the controlled pollination of seed parent 'C95-152' (unpatented) with pollen parent 'C00-09' (U.S. Plant Pat. No. 22,778). The new cultivar was discovered and selected as a single plant, breeder code M08-46-09, within a population of 100 resulting *Vaccinium* hybrid plants from this controlled pollination in October 2008 in a commercial field plantation environment at Lindendale, New South Wales, Australia. It was monitored over the next three years with five inspections per year to confirm consistency of traits. Selection criteria were, in combination, unique aromatic desirable tasting fruit produced in late season, firm, oblate shaped fruit, medium plant growth vigor, low chilling requirement, late time of vegetative bud burst and flowering, medium fruit size, medium yield, and small picking scar.

The selection was evaluated for a number of years at commercial farms at Lindendale, New South Wales, Australia.

Asexual reproduction of the new cultivar by cutting propagation since 2008 at Lindendale, New South Wales, Australia has demonstrated that the new cultivar reproduces true to type with all of the characteristics, as herein described, firmly fixed and retained through successive generations of such asexual propagation.

SUMMARY OF THE INVENTION

The new *Vaccinium* hybrid cultivar is a selection resulting from seedlings produced in a breeding programme of *Vaccinium* at Lindendale, NSW, Australia in August 2006 from the controlled pollination of seed parent 'C95-152' (unpatented) with pollen parent 'C00-09' (U.S. Plant Pat. No. 22,778).

Plants of the new cultivar differ from plants of the seed parent 'C95-152' primarily in having an upright to semi-upright plant growth habit, medium fruit yield and oblate shaped fruit with a desirable flavor whereas the seed parent has upright plant growth habit, round shaped fruit with a distinct, highly aromatic unpleasant flavor and low yield. Plants of the new cultivar differ from plants of the pollen parent 'C00-09' primarily in medium plant growth vigor, early to medium time of vegetative bud burst, early to medium time of first flowering, early to medium time of first fruit ripening, medium fruit size and round to slightly oblate fruit shape whereas the pollen parent has strong plant growth vigor, semi-upright to spreading plant growth habit and very large fruit size.

The following characteristics of the new cultivar have been repeatedly observed and can be used to distinguish 'RIDLEY 4609' as a new and distinct cultivar of *Vaccinium* hybrid plant:

1. Late time of vegetative bud burst
2. Late timing of beginning of flowering
3. Late timing of berry ripening
4. Medium plant growth vigor
5. Berry is firm
6. Picking scar is dry
7. Leaf width is broad
8. Berry size is medium
9. Berry sweetness and acidity making a unique aromatic desirable tasting fruit
10. Bloom on berry is weak to medium
11. Dark blue berry color Plants of the new cultivar differ from plants of the seed parent 'C95-152' primarily in having an upright to semi-upright plant growth habit, medium fruit yield and oblate shaped fruit with a desirable flavor whereas the seed parent has upright plant growth habit, round shaped fruit with a distinct, highly aromatic unpleasant flavor and low yield. Plants of the new cultivar differ from plants of the pollen parent 'C00-09' primarily in medium plant growth vigor, early to medium time of vegetative bud burst, early to medium time of first flowering, early to medium time of first fruit ripening, medium fruit size and round to slightly oblate fruit shape whereas the pollen parent has strong plant growth vigor, semi-upright to spreading plant growth habit and very large fruit size.

BRIEF DESCRIPTION OF THE DRAWINGS

The accompanying photographic illustration shows typical specimens in full color of the foliage and fruit of a 4 year old plant of the new variety 'Ridley 4609'. The colors are as nearly true as is reasonably possible in a color representation of this type.

Figure 1:
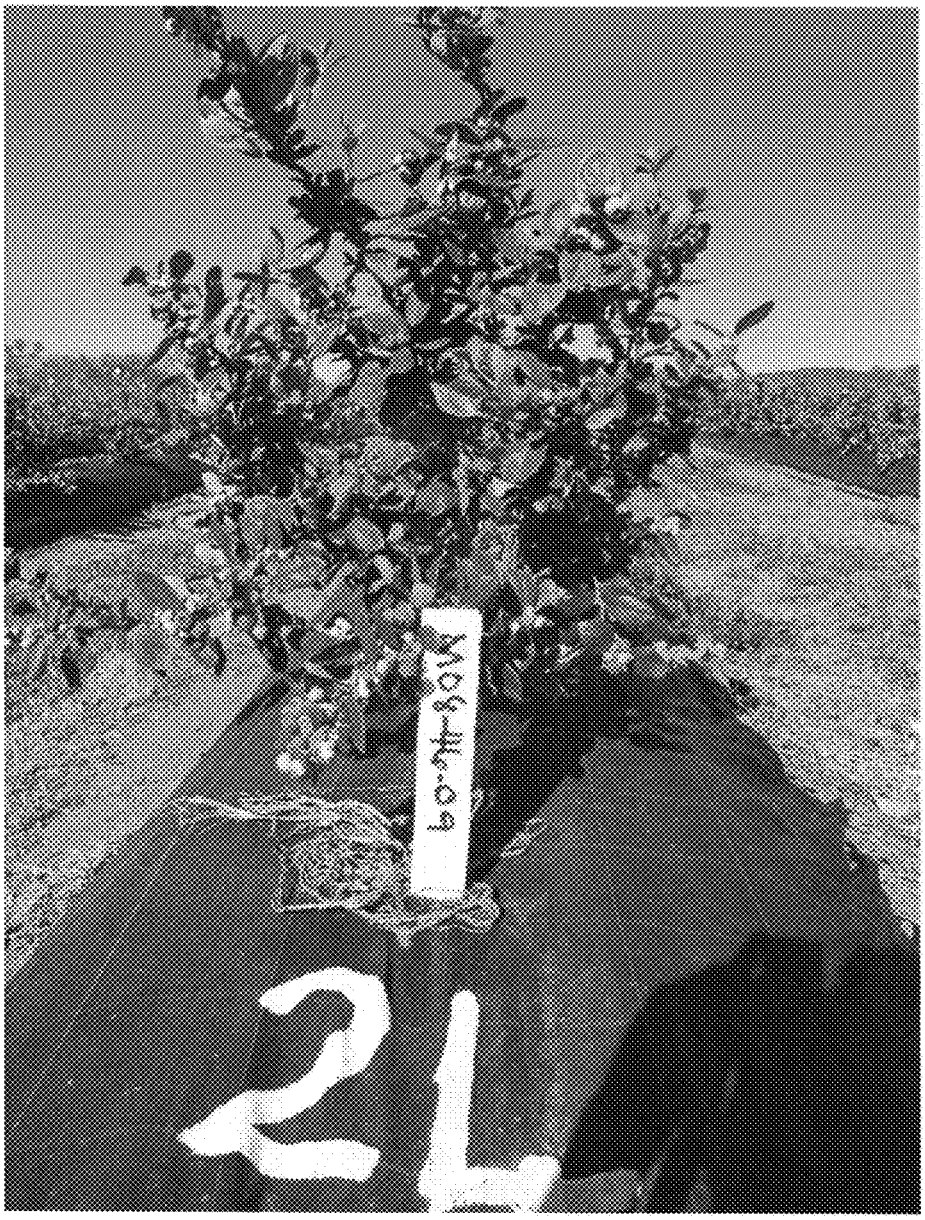
FIG. 1 is a photograph of the new variety 'Ridley 4609', demonstrating the plant's growth habit and fruit set.
Figure 2:
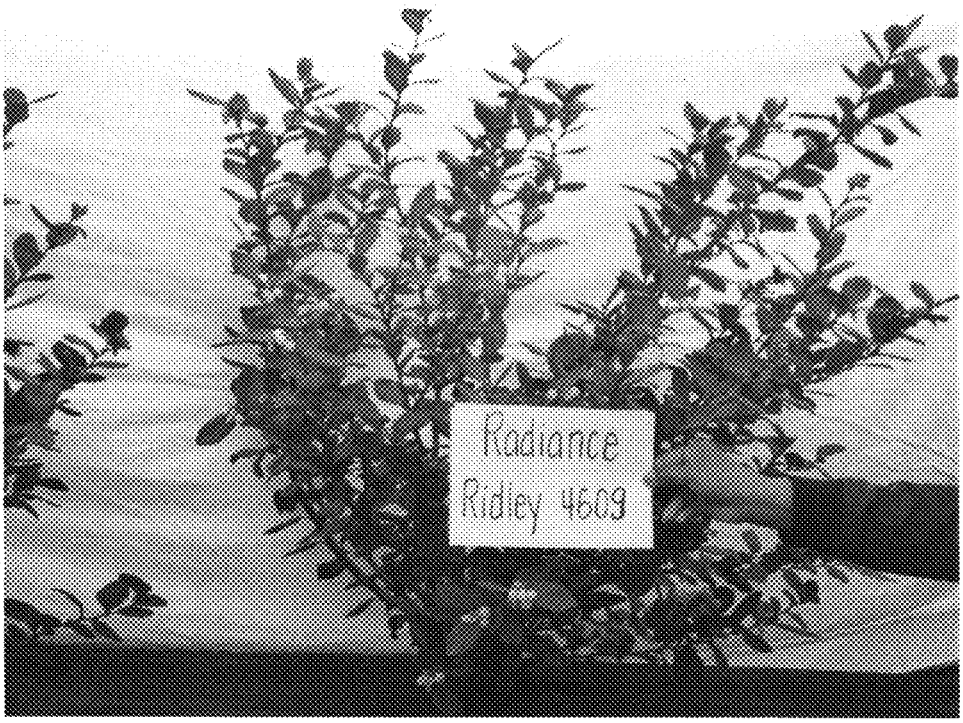
FIG. 2 is a photograph of the flowering plant of the new variety 'Ridley 4609'.
Figure 3:
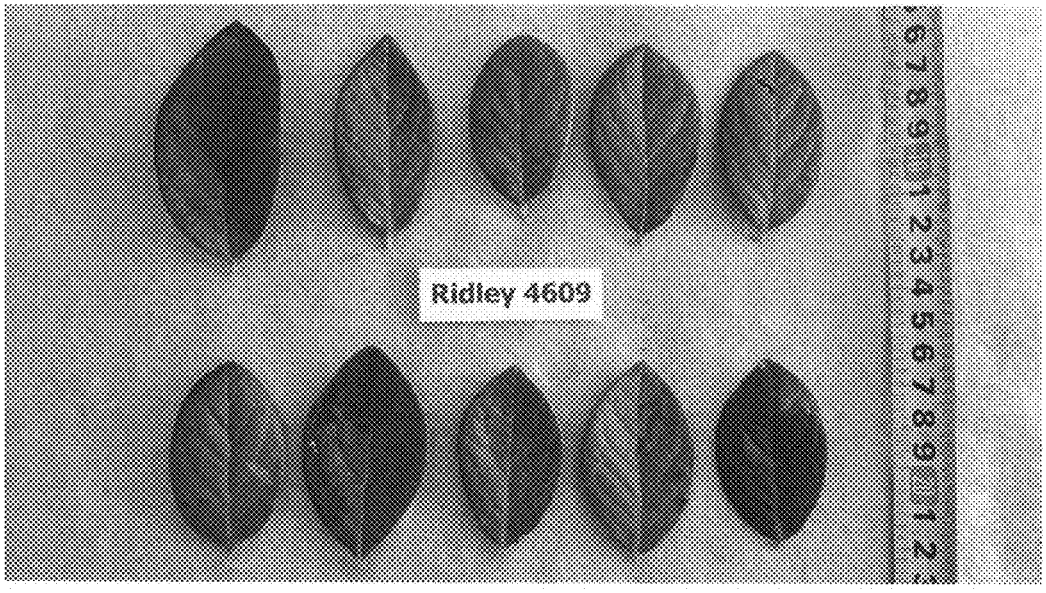
FIG. 3 is a photograph of the leaves of the new variety 'Ridley 4609'.
Figure 4:
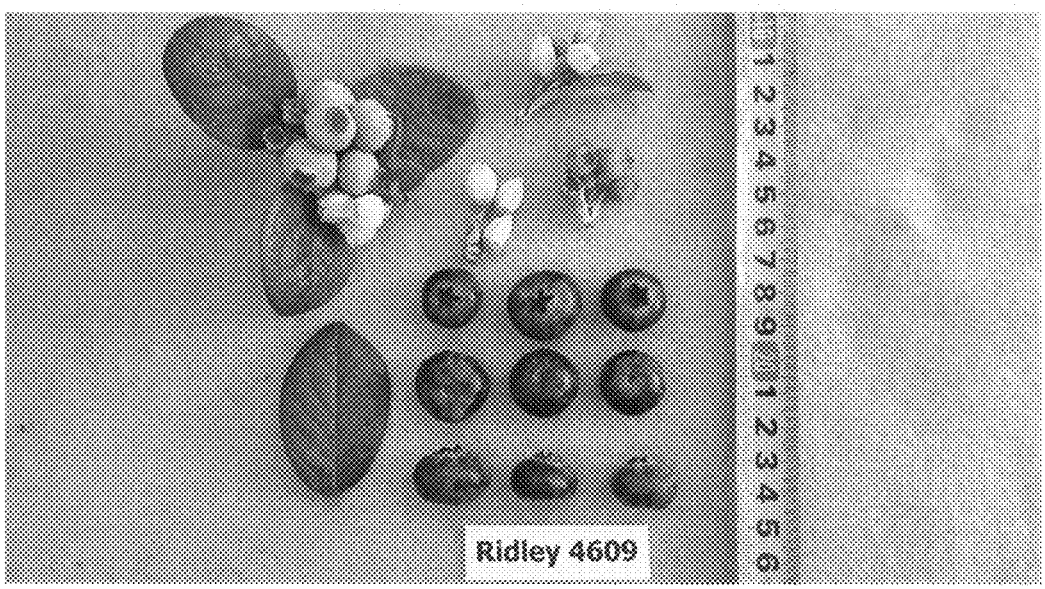
FIG. 4 is a photograph of the flower, leaf and fruit of the new variety 'Ridley 4609'.
Figure 5:
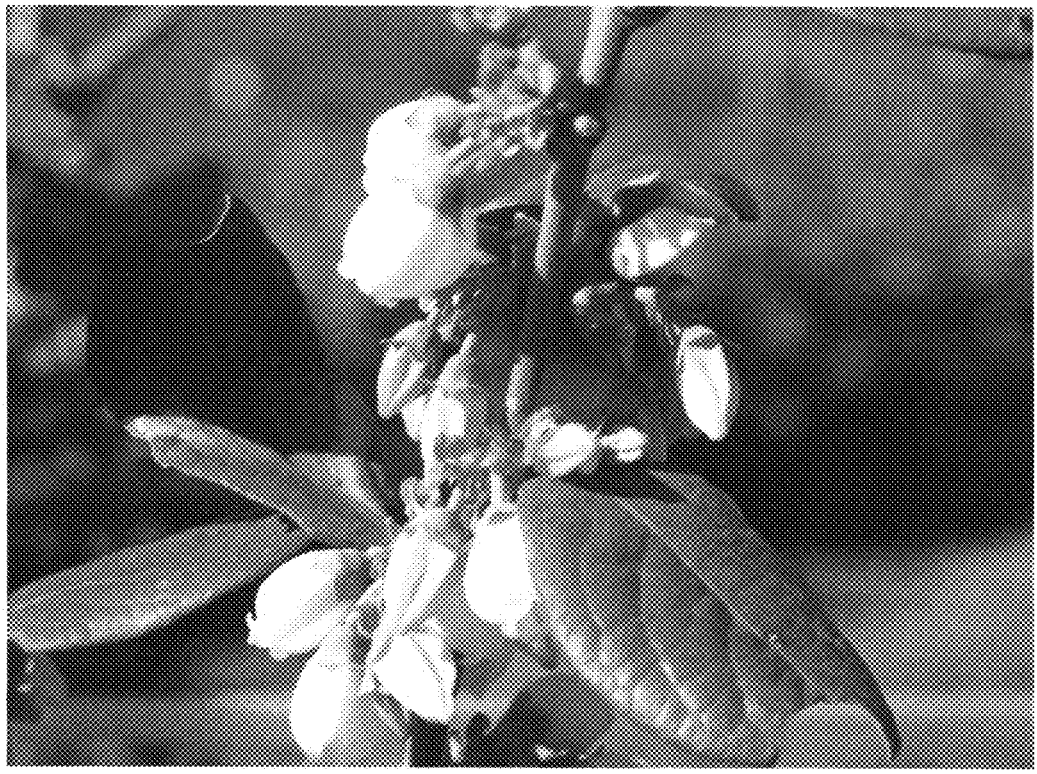
FIG. 5 is a photograph of the inflorescence and flower of the new variety 'Ridley 4609'.
Figure 6:
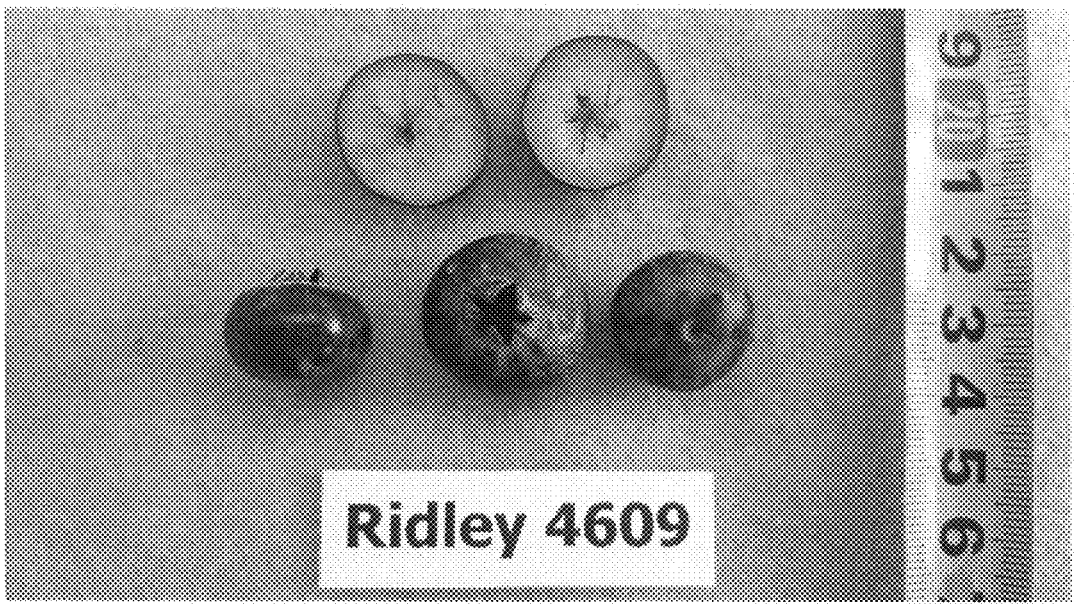
FIG. 6 is a photograph of the fruit detail of the new variety 'Ridley 4609'.

The colors in the photographs are as close as possible with the photographic and printing technology utilized. The color values cited in the detailed botanical description accurately describe the colors of the new blueberry.

DETAILED BOTANICAL DESCRIPTION

The following detailed description sets forth the distinctive characteristics of 'Ridley 4609'. The data that define these characteristics were collected from asexual reproductions of the original selection. Dimensions, sizes, colors, and other characteristics are approximations and averages set forth as accurately as possible. The plant history was taken on plants approximately 4 years of age, and the descriptions relate to plants grown in the field in Tabulam, New South Wales, Australia. Descriptions of fruit characteristics were made on fruit grown in Tabulam, New South Wales, Australia. Color designations are from Tabulam, New South Wales, Australia. Color notations are based on *The Royal Horticultural Society Colour Chart*, of The Royal Horticultural Society, London, 2007 edition.

Classification:

a. *Family*.—Ericaceae.
b. *Genus*.—*Vaccinium*.
c. *Species*.—hybrid.
d. *Common name*.—Southern Highbush Blueberry.

Parentage:

a. *Female parent*.—'C95-152' (unpatented).
b. *Male parent*.—'C00-09' (U.S. Plant Pat. No. 22,778).
c. *Market class*.—A fruiting plant intended for use as fresh fruit for shipping, customer pick and processing markets and as a home garden plant.

PLANT

General:

a. *Parentage*.—Female Parent — 'C95-152' (unpatented). Male Parent — 'C00-09' (U.S. Plant Pat. No. 22,778).
b. *Plant height*.—1.5 m.
c. *Plant width*.—1.2 m.
d. *Growth habit*.—Upright to semi-upright.
e. *Growth*.—Medium vigor.
f. *Productivity*.—4 kg per season from 3-4 year old plants planted at 3.0 m×0.9 m density.
g. *Cold hardiness*.—Has not been grown in all environments including harsh winter environments.
h. *Cold tolerance*.—Cold tolerance is expected to be low.
i. *Chilling requirement*.—Has not been grown in all environments and is typically grown as an evergreen crop where chilling hours are not important. 'Ridley 4609' is classed as 'low chill', typical of Southern Highbush Blueberry varieties with an estimated chilling requirement of 400 hours (not tested).
j. *Tolerance to disease*.—Moderate resistance to root disease (*Phytophthora* spp) and good resistance to blueberry rust.
k. *Leafing*.—Vegetative bud burst is late when grown as an evergreen in Australia.
l. *Twigginess*.—Low.

STEM

General:

a. *Suckering tendency*.—Low. Plants typically have 5-7 major canes per plant from a base 25 cm in diameter on 4 year old plants.
b. *Mature cane color*.—Color greyed orange 198C.
c. *Mature cane length*.—0.8-0.9 m.
d. *Mature cane width*.—1.2 cm.
e. *Bark texture*.—Medium roughness (typical of species).

f. *Fall color on new shoots*.—Crimson (approximately greyed purple N186C to 187A). Colors are variable subject to conditions of environment and culture.
g. *Surface texture of new wood*.—Smooth.
h. *Internode length on strong, new shoots*.—15-20 mm.
i. *Fruiting wood*.—To 15 cm in length.

FOLIAGE

General:
a. *Time of beginning of leaf bud burst*.—Late (late September to early October), in Australia.
b. *Leaf color* (*top side*).—Yellow green 147A.
c. *Leaf color* (*under side*).—Yellow green 147C.
d. *Leaf arrangement*.—Alternate.
e. *Leaf shape*.—Elliptic.
f. *Leaf margins*.—Entire.
g. *Undulation of margin*.—Weak.
h. *Leaf venation*.—Reticulate.
i. *Leaf apices*.—Acuminate.
j. *Leaf bases*.—Obtuse.
k. *Leaf length*.—52-75 mm.
l. *Leaf width*.—31-38 mm.
m. *Leaf length/width ratio*.—Medium (approximately 1).
n. *Leaf nectaries*.—Absent.
o. *Pubescence of upper side*.—Absent to very weak.
p. *Pubescence of lower side*.—Absent.
q. *Cross sectional profile*.—Flat.
r. *Longitudinal profile*.—Straight.
s. *Attitude*.—Horizontal.

Petioles:
a. *Length*.—1.0 to 3.0 mm.
b. *Width*.—2.0 mm.
c. *Color*.—Yellow green 146C-147C.

FLOWERS

General:
a. *Time of beginning of flowering*.—Late (late September to early November at Lindendale, NSW Australia).
b. *Time of* 50% *anthesis*.—Late October at Lindendale, NSW Australia.
c. *Flower shape*.—Urceolate.
d. *Flower bud density*.—Medium density.
e. *Flower fragrance*.—Weak.

Corolla:
a. *Color*.—White NN155D.
b. *Length*.—10-12 mm.
c. *Width*.—7-8 mm.
d. *Aperture width*.—2-3 mm.
e. *Anthocyanin coloration of corolla*.—Absent.
f. *Corolla ridges*.—Present.
g. *Protrusion of stigma*.—Absent.

Inflorescence:
a. *Length*.—25 to 35 mm.
b. *Diameter*.—18 to 20 mm.
c. *Length of peduncle*.—20-25 mm.
d. *Surface texture of peduncle*.—Smooth.
e. *Color of peduncle*.—146C.
f. *Length of pedicel*.—7-9 mm.
g. *Surface texture of pedicel*.—Smooth.
h. *Color of pedicel*.—147C.
i. *Number of flowers per cluster*.—5-7.
j. *Flower cluster density*.—Medium.

Calyx (with sepals):
a. *Diameter*.—9-12 mm.
b. *Color* (*sepals*).—Green 138C to yellow green 147C.

Stamen:
a. *Length*.—4-5 mm.
b. *Number per flower*.—Approximately 10.
c. *Filament color*.—Yellow green 144D.

Pistil:
a. *Length*.—10.20 mm.
b. *Style*.—Length — 5-6 mm.
c. *Ovary color* (*exterior*).—Yellow green 144D-147C.

Anther:
a. *Length*.—3.0-3.5 mm.
b. *Number*.—Approximately 10.
c. *Color*.—Grayed orange 167C-D.

Pollen:
a. *Abundance*.—Medium.
b. *Color*.—Grayed orange 167C-D.
c. *Self-compatibility*.—100% fruit set (Considered self-compatible).

FRUIT

General:
a. *Time of fruit ripening*.—Late (late October to mid December) at Lindendale, NSW Australia).
b. *Time of* 50% *maturity*.—Mid-November.
c. *Fruit development period*.—55 days.
d. *Cluster density*.—Medium to dense, 5-8 berries per cluster.
e. *Unripe fruit color*.—Green 138A.
f. *Ripe berry color*.—Black 202A.
g. *Berry surface wax abundance*.—Strong.
h. *Berry flesh color*.—Grayed green 194A-195A.
i. *Berry weight*.—2.9-3.1 g.
j. *Berry height from calyx to scar*.—13-16 mm.
k. *Berry diameter*.—19 mm.
l. *Berry shape*.—Oblate.
m. *Fruit stem scar*.—Small (dry).
n. *Sweetness when ripe*.—Medium to high (approximately 15-16% Brix).
o. *Firmness when ripe*.—Firm.
p. *Acidity when ripe*.—Medium to high (similar to 'Ridley 1403' (U.S. Plant Pat. No. 25,432) and 'Ridley 1812' (not patented) and higher than 'Ridley 1111' (U.S. Plant Pat. No. 23,572)).
q. *Storage quality*.—Good, lasted 10 weeks at 2 degrees Celcius in tests. Not tested with modified atmosphere storage yet.
r. *Suitability for mechanical harvesting*.—Shake requirement not yet tested.
s. *Self-fruitfulness*.—100% fruit set (considered self-compatible).
t. *Uses*.—Fresh fruit for shipping, customer pick and processing markets and as a home garden plant.

SEED

General:
a. *Seed abundance in fruit*.—Abundant.
b. *Seed color*.—Greyed orange 174B.
c. *Seed dry weight*.—About 67 seeds/1 mg.
d. *Seed length*.—1.6-1.8 mm.

COMPARISON BETWEEN POLLEN PARENT AND COMMERCIAL CULTIVARS

TABLE 1

Comparison between pollen parent and commercial cultivars

| Organ | Context | Ridley 4408 (U.S. Application No. 14/999,950) | Ridley 4609 |
|---|---|---|---|
| Plant | vigour | medium | medium |
| Plant | growth habit | Upright to semi upright | Upright to semi upright |
| One-year-old shoot | colour | green | green |
| One-year-old shoot | length of internode | medium | medium |
| Leaf | length | long | medium to long |
| Leaf | width | broad | broad |
| Leaf | shape | elliptic | elliptic |
| Leaf | colour of upper side | green | green |
| Leaf | intensity of green colour on upper side | medium | medium |
| Leaf | margin | entire | entire |
| Flower bud | anthocyanin coloration | weak | weak |
| Flower | shape of corolla | urceolate | urceolate |
| Flower | size of corolla tube | medium | medium |
| Flower | anthocyanin colouration of corolla tube | absent or very weak | absent or very weak |
| Flower | ridges on corolla tube | present | present |
| Fruit cluster | density | medium to dense | medium |
| Unripe fruit | intensity of green colour | light | light |
| Fruit | size | medium | medium |
| Fruit | shape in longitudinal section | round | oblate |
| Fruit | attitude of sepals | erect | erect |
| Fruit | diameter of calyx basin | large | large |
| Fruit | depth of calyx basin | deep | deep |
| Fruit | intensity of bloom | strong | weak to medium |
| Fruit | colour of skin | dark blue | dark blue |
| Fruit | firmness | firm | firm |
| Fruit | sweetness | high | medium to high |
| Fruit | acidity | high | medium to high |
| Time of | vegetative bud burst | early to medium | late |
| Time of | beginning of flowering | early to medium | late |
| Time of | beginning of fruit ripening | early to medium | late |

TABLE 1-continued

Comparison between pollen parent and commercial cultivars

| Organ | Context | Ridley 1812 (not patented) | Ridley 1403 (U.S. Plant Pat. No. 25,432) | C00-09 (U.S. Plant Pat. No. 22,778) |
|---|---|---|---|---|
| Plant | vigour | medium | strong | strong |
| Plant | growth habit | upright | upright to semi-upright | upright to semi-upright |
| One-year-old shoot | colour | green | green | green |
| One-year-old shoot | length of internode | medium | medium | medium |
| Leaf | length | long to very long | long to very long | long |
| Leaf | width | broad | broad | broad |
| Leaf | shape | elliptic | elliptic | elliptic |
| Leaf | colour of upper side | green | green | green |
| Leaf | intensity of green colour on upper side | medium | medium | dark |
| Leaf | margin | entire | entire | entire |
| Flower bud | anthocyanin coloration | weak | weak | weak |
| Flower | shape of corolla | urceolate | urceolate | urceolate |
| Flower | size of corolla tube | medium | medium to large | medium to large |
| Flower | anthocyanin colouration of corolla tube | absent or very weak | absent or very weak | absent or very weak |
| Flower | ridges on corolla tube | present | present | present |
| Fruit cluster | density | medium | medium to dense | medium |
| Unripe fruit | intensity of green colour | light | light | light |
| Fruit | size | very large | very large | very large |
| Fruit | shape in longitudinal section | oblate | round | oblate |
| Fruit | attitude of sepals | erect | erect | erect |
| Fruit | diameter of calyx basin | large to very large | large | large |
| Fruit | depth of calyx basin | deep to very deep | deep | deep |
| Fruit | intensity of bloom | weak to medium | medium | medium to strong |
| Fruit | colour of skin | dark blue | dark blue | dark blue |
| Fruit | firmness | medium | medium | very firm |
| Fruit | sweetness | medium to high | low to medium | high |
| Fruit | acidity | medium to high | medium to high | low |
| Time of | vegetative bud burst | medium | early to medium | late |
| Time of | beginning of flowering | late | very early | late |
| Time of | beginning of fruit ripening | late | early to medium | late |

The invention claimed is:

1. A new and distinct variety of blueberry plant named 'RIDLEY 4609', substantially as illustrated and described herein.

* * * * *